United States Patent [19]

Alt

[11] 3,979,200
[45] Sept. 7, 1976

[54] N-NITROSO-N-PHOSPHONOMETHYL GLYCINE COMPOUNDS AND HERBICIDAL USE THEREOF

[75] Inventor: Gerhard H. Alt, Creve Coeur, Mo.

[73] Assignee: Monsanto Company, St. Louis, Mo.

[22] Filed: Apr. 11, 1975

[21] Appl. No.: 567,214

Related U.S. Application Data

[62] Division of Ser. No. 394,019, Sept. 4, 1973, Pat. No. 3,888,915.

[52] U.S. Cl. .................................................. 71/86
[51] Int. Cl.[2] ............................................. A01N 9/36
[58] Field of Search .......................... 71/86, 87, 121; 260/583 CC

[56] References Cited
UNITED STATES PATENTS

| | | | |
|---|---|---|---|
| 2,710,794 | 6/1955 | Barnsley | 71/70 |
| 3,455,675 | 7/1969 | Irani | 71/86 |
| 3,574,851 | 4/1971 | Hyatt | 71/121 |
| 3,799,758 | 3/1974 | Franz | 71/86 |
| 3,888,915 | 6/1975 | Alt | 71/86 |

*Primary Examiner*—Glennon H. Hollrah
*Attorney, Agent, or Firm*—William T. Black; Donald W. Peterson

[57] ABSTRACT

N-Nitroso-N-phosphonomethylglycine compounds have been produced by the reaction of an inorganic nitrite and N-phosphonomethylglycine. These compounds are useful as post-emergent herbicides.

4 Claims, No Drawings

N-NITROSO-N-PHOSPHONOMETHYL GLYCINE COMPOUNDS AND HERBICIDAL USE THEREOF

This is a division of application Ser. No. 394,019 filed Sept. 4, 1973 now U.S. Pat. No. 3,888,915.

This invention relates to N-nitroso-N-phosphonomethyl glycine compounds, the preparation thereof, and their use as herbicides and in herbicidal compositions.

The N-nitroso-N-phosphonomethylglycine compounds of this invention are those having the formula

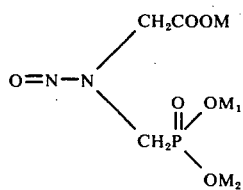

wherein M, $M_1$ and $M_2$ are each individually hydrogen or a salt-forming cation selected from the group consisting of alkali metals, alkaline earth metals, ammonium, aliphatic ammonium and phenyl ammonium with the proviso that at least one of M, $M_1$ or $M_2$ is H when the others are ammonium, aliphatic ammonium or phenyl ammonium.

The term "alkali-metal" encompasses lithium, sodium, potassium, cesium and rubidium; and the term "alkaline earth metal" includes beryllium, magnesium calcium, strontium and barium.

The term "aliphatic ammonium" as employed herein encompasses mono-, di- and tri-alkyl ammonium groups wherein the alkyl groups contain from 1 to 6 carbon atoms as well as the cycloalkyl groups containing from 3 to 6 carbon atoms. The term "phenyl ammonium" as employed herein encompasses aniline and substituted anilines such as the mono-, di- and tri-halo, nitro, methoxy, methyl, and ethyl anilines.

The aliphatic ammonium group includes, for example, mono-, di- and tri-methyl, ethyl, propyl, isopropyl, butyl, pentyl, hexyl, t-butyl, t-pentyl ammonium groups as well as cyclopropyl ammonium, cyclobutylethylammonium, cyclopentylmethyl ammonium, cyclohexylammonium and the like.

Illustrative of the phenyl ammonium group are those derived from the primary phenyl amines such as aniline, methoxyaniline, ethoxyaniline, o,m,p-toluidine, o,m,p-chloroaniline, o,m,p-anisidine,o,m, and p-nitroaniline, 2,4-dichloroaniline, 3,5-dichloroaniline, 2,5-diiodoaniline, o,m, and p-bromoaniline and the like.

The compunds of the instant invention are produced by the reaction of N-phosphonomethylglycine with a nitrite salt in an aqueous media. For example, the monosodium salt of N-nitroso-N-phosphonomethylglycine is produced by reacting approximately equal molar quantities of sodium nitrite with N-phosphonomethylglycine. The free acid can then be prepared by acidification of the acid mixture with an acid such as hydrochloric acid. The ammonium and other salts can then be produced by neutralization with the appropriate base or by reacting the salt with ammonium chloride or an amine hydrochloride salt.

Nitrites which can be employed in this process include the alkali metal and alkaline metal nitrites.

In conducting the process of the instant invention, the ratio of the alkali metal nitrite to the N-phosphonomethyl glycine is not narrowly critical and can be varied over a wide range, i.e., from about 1 to 10 to 10 to 1. Of course, it is preferred to employ the alkali nitrite and the N-phosphonomethyl glycine in approximately equimolar amounts, i.e., molar ratio of about 1.05–1 to 1–1.05 in as much as a large excess of one over the other renders the separation of the product more difficult.

The temperature at which the process is conducted can vary from about 0°C. to 70°C. It is preferred for convenience to conduct the process at a temperature of from about 5°C. to about 30°C.

The process of the instant invention is preferably conducted in an aqueous medium so the inorganic nitrite and N-phosphonomethylglycine are contacted in solution.

The compounds and compositions of the present invention find use as herbicides and phytoxicants.

The following examples serve to further illustrate the invention. All parts are parts by weight unless otherwise expressly set forth.

EXAMPLE 1

N-phosphonomethylglycine (0.02 moles) was suspended in water (20 ml.) in a glass reactor. Sodium nitrite (0.02 moles) dissolved in water ( ml.) was added dropwise with stirring. The reaction mixture was stirred at room temperature for 3 hours and then aniline hydrochloride (0.02 moles) in water was added. A small amount of ethanol (approximately 7 cc) was added and a solid crystallized. The solid was removed by filtration, yielding 2.1 gms. of a material (m.p. 173°–175°C. with decomposition) identified as N-nitroso-N-phosphonomethylglycine aniline salt by nuclear magnetic resonance spectral analysis.

EXAMPLE 2

N-Phosphonomethylglycine (16.9 g., 0.1 mole) was suspended in water (40 ml.) in a glass reactor and sodium nitrite (7.0 g., 0.1 mole) dissolved in water (20 ml.) was added dropwise with stirring. The reaction mixture was stirred until homogenous, allowed to stand overnight. The reaction mixture was filtered and washed into a 100 ml. flask to give a 1 molar aqueous solution of the monosodium salt of N-nitroso-N-phosphonomethylglycine.

EXAMPLE 3

The post-emergent herbicidal activity of various compounds of this invention is demonstrated as follows. The active ingredients are applied in spray from to 21-day old specimens of various plant species. The spray, a water solution containing the active ingredient and a surfactant (1% by weight), is applied to the plants in different sets of pans at several rates (pounds per acre) of active ingredient. The treated plants are placed in a greenhouse and the effects observed after approximately 4 weeks. The results are shown in Table I.

The post-emergence herbicidal activity index used in Table I is as follows:

| % CONTROL | RATING |
|---|---|
| 0 – 24 | 0 |
| 25 – 49 | 1 |

| % CONTROL | RATING |
|---|---|
| 50 – 74 | 2 |
| 75 – 99 | 3 |
| 100% | 4 |

The plant species utilized in these tests are identified by letter in accordance with the following legend:

A — Canada Thistle
B — Nutsedge
C — Quackgrass
D — Johnsongrass
E — Cocklebur
F — Velvetleaf
G — Morningglory
H — Lambsquarters
I — Smartweed
J — Downy brome
K — Barnyardgrass

TABLE I

| Compound of Example I | Rate lb/acre | A | B | C | D | E | F | G | H | I | J | K |
|---|---|---|---|---|---|---|---|---|---|---|---|---|
| | 1/8 | 0 | 0 | 1 | 0 | 1 | 1 | 1 | 1 | 1 | 0 | 2 |
| | 1.4 | 1 | 0 | 1 | 0 | 2 | 1 | 2 | 2 | 0 | 1 | 2 |
| | 1/2 | 2 | 1 | 2 | 1 | 2 | 2 | 2 | 4 | 1 | 1 | 2 |
| | 1.0 | 2 | 2 | 3 | 2 | 2 | 2 | 2 | 3 | 2 | 1 | 3 |
| | 4 | 4 | 1 | 3 | 1 | 2 | 2 | 2 | 4 | 4 | 2 | 4 |
| | 10 | 4 | 2 | 4 | 2 | 2 | 2 | 2 | 4 | 1 | 4 | 4 |
| Compound of Example II | 4 | 1 | 0 | 0 | 0 | 1 | 0 | 1 | 0 | 0 | 0 | 1 |

Other compounds included within the scope of this invention which can be produced by the methods set forth in the preceding examples are, for example:

Disodium salt of N-nitroso-N-phosphonomethylglycine
Monopotassium salt of N-nitroso-N-phosphonomethylglycine
Dipotassium salt of N-nitroso-N-phosphonomethylglycine
Tripotassium salt of N-nitroso-N-phosphonomethylglycine
Trisodium salt of N-nitroso-N-phosphonomethylglycine
Monomethylamine salt of N-nitroso-N-phosphonomethylglycine
Monodiisopropylamine salt of N-nitroso-N-phosphonomethylglycine
Monodiethanolamine salt of N-nitroso-N-phosphonomethylglycine
Hemicalcium salt of N-nitroso-N-phosphonomethylglycine
Calcium salt of N-nitroso-N-phosphonomethylglycine
Hemimagnesium salt of N-nitroso-N-phosphonomethylglycine
Magnesium salt of N-nitroso-N-phosphonomethylglycine
Hemicopper salt of N-nitroso-N-phosphonomethylglycine
Monolithium salt of N-nitroso-N-phosphonomethylglycine
Dilithium salt of N-nitroso-N-phosphonomethylglycine
Trilithium salt of N-nitroso-N-phosphonomethylglycine
Barium salt of N-nitroso-N-phosphonomethylglycine
Monoammonium salt of N-nitroso-N-phosphonomethylglycine
Mono-o-toluidine salt of N-nitroso-N-phosphonomethylglycine
Mono-m-toluidine salt of N-nitroso-N-phosphonomethylglycine
Mono-p-toluidine salt of N-nitroso-N-phosphonomethylglycine
Monocyclohexylamine salt of N-nitroso-N-phosphonomethylglycine
Monomorpholine salt of N-nitroso-N-phosphonomethylglycine
Monoethanolamine salt of N-nitroso-N-phosphonomethylglycine
Monoethylamine salt of N-nitroso-N-phosphonomethylglycine
Monodimethylamine salt of N-nitroso-N-phosphonomethylglycine and aniline salts indicated on page 3 of application.

The compounds of the present invention show postemergent herbicidal activity when applied at a rate of from 2 to 25 pounds per acre on species such as morningglory, Johnsongrass, barnyardgrass, lambsquarters and velvetleaf.

In employing the products of the invention as herbicides, the active ingredients, that is, the product of this invention can be used alone or in combination with a material referred to in the art as an adjuvant in liquid or solid form. Herbicidal formulations are prepared by admixing the ingredient with an adjuvant including diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The herbicidal formulations usually contain from about 0.01 percent to about 99 percent by weight of active ingredient.

Typical finely-divided solid carriers and inert solid extenders which can be used with the active ingredients include, for example, the talcs, natural and synthetic clays (e.g. kaolinites and attapulgite), pumice, silica, synthetic calcium and magnesium silicates, diatomaceous earth, quartz, Fuller's earth, salt, sulfur, powdered cork, powdered wood, ground corn cobs, walnut flour, chalk, tobacco dust, charcoal, volcanic ash, cottonseed hulls, wheat flour, soybean flour, tripoli and the like. Typical liquid diluents include for example; petroleum fractions such as kerosene, hexane, xylene, benzene, Diesel Oil, toluene, acetone, ethylene dichloride, Stoddard solvent, alcohols such as propanol, glycols and the like.

Herbicidal formulations, particularly liquids and wettable particles, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein.

Specific surface-active agents which can be used in the herbicidal formulations of this invention are set out, for example, in Searle U.S. Pat. No. 2,426,417, Todd U.S. Pat. No. 2,655,447, Jones U.S. Pat. No. 2,412,510 and Lenher U.S. Pat. No. 2,139,276. A detailed list of such agents is also set forth by J. W. McCutcheon in an article in "Soap and Chemical Specialties", Vol. 31, No. 7, pages 50–61; see also McCutcheon article in "Chemical Industries", November, 1947, page 811 et seq., entitled "Synthetic Detergents"; "Detergents and Emulsifiers — Up to Date" (1960), by J. W. McCutcheon, Inc., and Bulletin E-607 of the Bureau of Entomology and Plant Quarantine of the U.S.D.A. In general, less than 50 parts by weight of the surface active agent is present per 100 parts by weight of phytotoxic formulation.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylinic glycols, polyoxyethylene derivatives of alkylphenols (particularly isooctylphenol and nonylphenyl) and polyoxyethylene derivatives of the mono-higher fatty esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) taurates.

Wettable powder formulations usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total formulation. Where, required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Dusts are dense finely-divided particulate formulations which are intended for application to the soil in dry form. Dusts are characterized by their free-flowing and rapid settling properties so that they are not readily wind-borne to areas where they are of no value. Dusts contain primarily an active ingredient and a dense, free-flowing finely-divided particulate extender. However, their performance is sometimes aided by the inclusion of a wetting agent such as those listed hereinbefore under wettable powder compositions and convenience in manufacture frequently demands the inclusion of an inert, absorptive grinding aid. Suitable classes of grinding aids are natural clays, diatomaceous earth and synthetic minerals derived from silica or silicate. Preferred grinding aids include attapulgite clay, diatomaceous silica, synthetic fine silica and synthetic calcium and magnesium silicates.

The inert finely-divided solid extender for the dusts can be either of vegetable or mineral origin. The solid extenders are characterized by possessing relatively low surface areas and are poor in liquid absorption. Suitable inert solid extenders for herbicidal dusts include micaceous talcs, pyrophyllite, dense kaolin clays, ground calcium phosphate rock and tobacco dust. The dusts usually contain from about 0.5 to 95 parts active ingredient, 0 to 50 parts grinding aid, 0 to 50 parts wetting agent and 5 to 99.5 parts dense solid extender, all parts being by weight and based on the total weight of the dust.

The wettable powders described above may also be used in the preparation of dusts. While such wettable powders could be used directly in dust form, it is more advantageous to dilute them by blending with the dense dust diluent. In this manner, dispersing agents, corrosion inhibitors, and antifoam agents may also be found as components of a dust.

Granules are physically stable particulate formulations comprising active ingredient adhering to or distributed through a basic matrix of an inert, finely-divided particulate extender. In order to aid leaching of the active ingredient from the particulate, a surface active agent such as those listed hereinbefore under wettable powders can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely-divided clays such as kaolin clays, hydrated attapulgite or bentonitic clays. These extenders are sprayed or blended with the active ingredient to form the herbicidal formulations.

The mineral particles which are used in the herbicidal formulations usually have a size range of 10 to 100 mesh, but preferably such that a large majority of the particles have from 14 to 60 mesh with the optimum size being from 20 to 40 mesh. Clay having substantially all particles between 14 and 80 mesh and at least about 80 percent between 20 and 40 mesh is particularly preferred for use in the herbicidal formulations. The term "mesh" as used herein means U.S. Sieve Series.

The granular herbicidal formulations generally contain from about 5 parts to about 30 parts by weight of active ingredient per 100 parts by weight of clay and 0 to about 5 parts by weight of surface active agent per 100 parts by weight of particulate clay. The preferred granular formulations contain from about 10 parts to about 25 parts by weight of active ingredient per 100 parts by weight of clay.

The herbicidal compositions produced from the products of this invention can also contain other additaments, for example, fertilizers, phytotoxicants, other plant growth regulants, pesticides and the like used as adjuvant or in combination with any of the above-described adjuvants. Chemicals useful in combination with the active ingredients of this invention include for example, ureas, carbamates, acetamides, acetanilides, uracils, acetic acids, phenols, thiolcarbamates, triazoles, benzoic acids, nitriles and the like.

What is claimed is:

1. A herbicidal method which comprises contacting a plant with a herbicidally effective amount of a compound having the formula

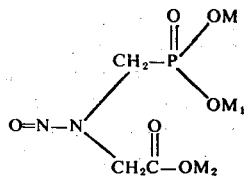

wherein M, M₁ and M₂ are each individually hydrogen or a salt-forming cation selected from the class consisting of alkali metals, alkaline earth metals, ammonium, aliphatic ammonium or phenyl ammonium.

2. The herbicidal method of claim 1 wherein $M_1$ is an aliphatic ammonium group and M and $M_2$ are hydrogen.

3. The herbicidal method of claim 1 wherein the phenyl ammonium group is an anilino group.

4. The herbicidal method of claim 1 wherein $M_1$ is sodium and M and $M_2$ are hydrogen.

* * * * *